US009005953B2

(12) United States Patent
Muramatsu et al.

(10) Patent No.: US 9,005,953 B2
(45) Date of Patent: Apr. 14, 2015

(54) RECOMBINANT MICROORGANISM HAVING BUTANOL PRODUCTION CAPACITY AND BUTANOL PRODUCTION METHOD

(75) Inventors: Masayoshi Muramatsu, Nishikamo-gun (JP); Shusei Obata, Nagoya (JP); Satoshi Yoneda, Toyota (JP); Masahiro Sugimura, Toyota (JP); Tomohisa Kuzuyama, Setagaya-ku (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 693 days.

(21) Appl. No.: 12/775,048

(22) Filed: May 6, 2010

(65) Prior Publication Data

US 2010/0285549 A1    Nov. 11, 2010

(30) Foreign Application Priority Data

May 8, 2009   (JP) ................ 2009-113632

(51) Int. Cl.
*C12N 1/21* (2006.01)
*C12P 7/16* (2006.01)
*C12N 9/02* (2006.01)
*C12N 9/10* (2006.01)

(52) U.S. Cl.
CPC .............. *C12P 7/16* (2013.01); *C12N 9/0004* (2013.01); *C12N 9/1029* (2013.01); *Y02E 50/10* (2013.01)

(58) Field of Classification Search
CPC ........ C12N 9/0004; C12N 9/1029; C12P 7/16
USPC ............................ 435/252.33, 160
See application file for complete search history.

(56) References Cited

U.S. PATENT DOCUMENTS 6,358,717 B1    3/2002   Blaschek et al.

FOREIGN PATENT DOCUMENTS

JP   2008-061506 A   3/2008
WO  2008/080124 A2   7/2008
WO  2008/137402 A1   11/2008

OTHER PUBLICATIONS

Witkowski et al. (Biochemistry. Sep. 7, 1999; 38(36): 11643-50.*
Shota Atsumi et al., "Metabolic Engineering of *Escherichia coli* for 1-Butanol Production", Metabolic Engineering, (2008), vol. 10, pp. 305-311, Department of Chemical and Biomolecular Engineering, University of California, Los Angeles, CA, USA.
Masayuki Inui, et al., "Expression of *Clostridium acetobutylicum* Butanol Synthetic Genes in *Escherichia coli*", Applied Genetics and Molecular Biotechnology, (2008), vol. 77, pp. 1305-1316, published online.
W. Andersch et al., Acetone-Butanol Production by *Clostridium acetobutylicum* in an Ammonium-Limited Chemostat at Low PH Values, Biotechnology Letters, 1982, pp. 29-32 vol. 4 1.
Stanley N. Cohen et al., Non chromosomal Antibiotic Resistance in Bacteria: Genetic Transformation of *Escherichia coli* by R-factor DNA, Proc. Nat. Acad. Sci. USA, Aug. 1972, pp. 2110-2114, vol. 69, No. 8.
Daniel M. Becker et al., High-Efficiency Transformation of Yeast by Electroporation, Methods in Enzymology, Cloning and Recombinant DNA, 1991, pp. 182-187, vol. 194.
Albert Hinnen et al., Transformation of Yeast, Proc. Natl. Acad. Sci. USA, Apr. 1978, pp. 1929-1933, vol. 75, No. 4.
Hisao Ito et al., Transformation of Intact Yeast Cells Treated with Alkali Cations, Journal of Bacteriology, Jan. 1983, pp. 163-168, vol. 153, No. 1.

* cited by examiner

*Primary Examiner* — Tekchand Saidha
*Assistant Examiner* — MD. Younus Meah
(74) *Attorney, Agent, or Firm* — Sughrue Mion, PLLC

(57) ABSTRACT

This invention relates to a recombinant microorganism having improved butanol production capacity and butanol production with the use of such recombinant microorganism with good efficiency. In this invention, the acetoacetyl-CoA synthase gene encoding an enzyme capable of synthesizing acetoacetyl-CoA from malonyl-CoA and acetyl-CoA and a group of genes involved in butanol biosynthesis that enables synthesis of butanol from acetoacetyl-CoA are introduced into a host microorganism.

2 Claims, No Drawings

SEQUENCE LISTING

<160> NUMBER OF SEQ ID NOS: 11

<210> SEQ ID NO 1

<211> LENGTH: 329
<212> TYPE: PRT
<213> ORGANISM: Streptomyces sp.

<400> SEQUENCE: 1

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
            20                  25                  30

Asp Asp Trp Ile Thr Arg Lys Thr Gly Ile Arg Gln Arg Arg Trp Ala
        35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
    130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Ala Val Arg Ala Gly Ser
    290                 295                 300

Phe Arg Pro Gly Glu Leu Val Leu Leu Ala Gly Phe Gly Gly Gly Met
305                 310                 315                 320

Ala Ala Ser Phe Ala Leu Ile Glu Trp
                325

<210> SEQ ID NO 2
<211> LENGTH: 28
<212> TYPE: DNA
<213> ORGANISM: Artificial
<220> FEATURE:
<223> OTHER INFORMATION: synthetic DNA

<400> SEQUENCE: 2
atgaaagaag ttgtaatagc tagtgcag                                    28

<210> SEQ ID NO 3
<211> LENGTH: 26
<212> TYPE: DNA
<213> ORGANISM: Artificial
<220> FEATURE:
<223> OTHER INFORMATION: synthetic DNA

<400> SEQUENCE: 3
ctagcacttt tctagcaata ttgctg                                      26

<210> SEQ ID NO 4
<211> LENGTH: 26
<212> TYPE: DNA
<213> ORGANISM: Artificial
<220> FEATURE:
<223> OTHER INFORMATION: synthetic DNA

<400> SEQUENCE: 4
aaacatatga agaagttgt aatagc                                       26

<210> SEQ ID NO 5
<211> LENGTH: 28
<212> TYPE: DNA
<213> ORGANISM: Artificial
<220> FEATURE:
<223> OTHER INFORMATION: synthetic DNA

<400> SEQUENCE: 5
aaactcgagc tagcactttt ctagcaat                                    28

<210> SEQ ID NO 6
<211> LENGTH: 29
<212> TYPE: DNA
<213> ORGANISM: Artificial
<220> FEATURE:
<223> OTHER INFORMATION: synthetic DNA

<400> SEQUENCE: 6
aaacatatga ccgacgtccg attccgcat                                   29

<210> SEQ ID NO 7
<211> LENGTH: 29
<212> TYPE: DNA
<213> ORGANISM: Artificial
<220> FEATURE:
<223> OTHER INFORMATION: synthetic DNA

<400> SEQUENCE: 7
aaactcgagt taccactcga tcagggcga                                   29

<210> SEQ ID NO 8
<211> LENGTH: 30
<212> TYPE: DNA
<213> ORGANISM: Artificial
<220> FEATURE:
<223> OTHER INFORMATION: synthetic DNA

<400> SEQUENCE: 8
ctcccatgga actaaacaat gtcatccttg                                  30

<210> SEQ ID NO 9
<211> LENGTH: 38
<212> TYPE: DNA
<213> ORGANISM: Artificial

```
<220> FEATURE:
<223> OTHER INFORMATION: synthetic DNA

<400> SEQUENCE: 9
aacggatcct tattttgaat aatcgtagaa accttttc                              38

<210> SEQ ID NO 10
<211> LENGTH: 47
<212> TYPE: DNA
<213> ORGANISM: Artificial
<220> FEATURE:
<223> OTHER INFORMATION: synthetic DNA

<400> SEQUENCE: 10
cacgtcgaca aggagatata atgaaagtta caaatcaaaa agaacta                    47

<210> SEQ ID NO 11
<211> LENGTH: 46
<212> TYPE: DNA
<213> ORGANISM: Artificial
<220> FEATURE:
<223> OTHER INFORMATION: synthetic DNA

<400> SEQUENCE: 11
cacgcggccg cttaaaatga ttttatatag atatccttaa gttcac                     46
```

RECOMBINANT MICROORGANISM HAVING BUTANOL PRODUCTION CAPACITY AND BUTANOL PRODUCTION METHOD

BACKGROUND OF THE INVENTION

1. Field of the Invention

The present invention relates to a recombinant microorganism having butanol production capacity, in which a group of genes involved in butanol biosynthesis is incorporated, and a butanol production method using the recombinant microorganism.

2. Background Art

In recent years, depletion of petroleum resources and global reduction of carbon dioxide emission have been actively discussed. It is predicted that the petroleum price will sharply increase in the future. Therefore, development of alternative petroleum materials has been awaited. For instance, there have been attempts to bioconvert biomass, sugar, starch, fat and oil, proteins, and the like, which have been produced by plants from water and carbon dioxide, into alternative petroleum materials with the use of solar energy for practical use. An example of such an attempt involves the technology of producing plant-derived polylactic acid or polybutylene succinate as an alternative plastic material made from petroleum. Further, ethanol is obtained by fermentative production from sugar, starch, or the like and blended with automobile fuel purified from petroleum so as to be used in the U.S., Brazil, and other countries.

In addition, 1-butanol is an important compound that can be used as either fuel or resin material. U.S. Pat. No. 6,358,717 discloses production of acetone, 1-butanol, and ethanol with the use of bacteria such as *Clostridium acetobutylicum* and *Clostridium beijerinckii* (ABE fermentation).

However, it is difficult to obtain high-purity 1-butanol by fermentative production. At present, 1-butanol has been generally produced by chemical synthesis from petroleum. In recent years, it has been attempted to efficiently produce 1-butanol in *Escherichia coli* or yeast with the use of gene recombinant technology. For 1-butanol synthesis, it is necessary to carry out the following conversion steps described below in a microorganism. Specifically, the steps are as follows: (I) a step of converting acetyl-CoA into acetoacetyl-CoA; (II) a step of converting acetoacetyl-CoA into 3-hydroxybutyl-CoA; (III) a step of converting 3-hydroxybutyl-CoA into crotonyl CoA; (IV) a step of converting crotonyl CoA into butyryl-CoA; (V) a step of converting butyryl-CoA into butyraldehyde; and (VI) a step of converting butyraldehyde into butanol.

*Clostridium acetobutylicum*-derived genes have been known to be involved in the above conversion steps. There are examples of producing 1-butanol by causing the expression of such genes in *Escherichia coli* (approximately 60 mg/L) (see Metabolic Engineering, 10. 6. 305-311 (2008) and Appl. Microbiol. Biotechnol., 77, 1305-1316, 2008). In addition, there is another example of producing 1-butanol in *Escherichia coli* (approximately 75 mg/L) and in *Saccharomyces cerevisiae* (approximately 2 mg/L) with the use of the Euglena-derived TER gene and the *Clostridium beijerinckii*-derived ALD gene (WO2008-137402). In addition to the above, there is an example of producing 1-butanol in *Saccharomyces cerevisiae*. However, the production rate was approximately 20 mg/L (WO2008-080124).

As described above, the technology for producing 1-butanol in recombinant *Escherichia coli* or yeast with the use of the *Clostridium acetobutylicum*-derived gene has been under development. However, in such case, the productivity is lower than that in the case of production of 1-butanol, at a rate of approximately 2.5 g/L with the use of *Clostridium acetobutylicum* (Biotechnol. Lett., 4, 29-32, 1982). Therefore, an increase in the amount of a product produced in such a recombinant has been awaited.

SUMMARY OF THE INVENTION

Accordingly, in view of the above circumstances, it is an object of the present invention to provide a recombinant microorganism having excellent butanol production capacity and a butanol production method whereby butanol can be produced with the use of such recombinant microorganism with good efficiency.

As a result of intensive studies in order to achieve the above object, the present inventors have found that butanol productivity can be improved by using an enzyme capable of synthesizing acetoacetyl-CoA from malonyl-CoA and acetyl-CoA instead of thiolase capable of synthesizing acetoacetyl-CoA from two acetyl-CoA molecules or in addition to thiolase and allowing the enzyme to function in the aforementioned microorganism capable of synthesizing butanol from acetoacetyl-CoA synthesized from acetyl-CoA. This has led to the completion of the present invention.

The present invention encompasses the following.

(1) A recombinant microorganism, comprising an acetoacetyl-CoA synthase gene encoding an enzyme capable of synthesizing acetoacetyl-CoA from malonyl-CoA and acetyl-CoA and a group of genes involved in butanol biosynthesis that enables synthesis of butanol from acetoacetyl-CoA, wherein the genes are introduced into a host microorganism.

(2) The recombinant microorganism according to (1), wherein the acetoacetyl-CoA synthase gene is a gene from a microorganism of the genus *Streptomyces*.

(3) The recombinant microorganism according to (1), wherein the acetoacetyl-CoA synthase gene encodes a protein having the amino acid sequence of SEQ ID NO: 1 or a protein having an amino acid sequence with a 80% or more identity to the amino acid sequence of SEQ ID NO: 1 and having a function of synthesizing acetoacetyl-CoA from malonyl-CoA and acetyl-CoA.

(4) The recombinant microorganism according to (1), wherein the group of genes involved in butanol biosynthesis consists of the β-hydroxybutyryl-CoA dehydrogenase gene, the 3-hydroxybutyryl-CoA dehydratase gene, the butyryl-CoA dehydrogenase gene, the butyraldehyde dehydrogenase gene, and the butanol dehydrogenase gene.

(5) The recombinant microorganism according to (1), wherein the group of genes involved in butanol biosynthesis includes a gene from a microorganism of the genus *Clostridium*, which has butanol biosynthesis capacity.

(6) The recombinant microorganism according to (5), wherein the microorganism of the genus *Clostridium* is *Clostridium acetobutylicum*.

(7) The recombinant microorganism according to (1), wherein the host microorganism is *Escherichia coli*.

(8) A butanol production method, comprising culturing a recombinant microorganism according to any one of (1) to (7) and collecting butanol from the medium.

EFFECTS OF THE INVENTION

According to the present invention, the butanol production efficiency of a recombinant microorganism having butanol production capacity can be significantly improved. Specifically, the recombinant microorganism of the present invention has more excellent butanol production capacity than a conventional recombinant microorganism having butanol production capacity. Therefore, the use of the recombinant microorganism of the present invention results in the improvement of productivity upon production of butanol used as fuel or resin material, allowing butanol production cost reduction.

DESCRIPTION OF THE PREFERRED EMBODIMENTS

Hereinafter, the present invention is described in detail.

The recombinant microorganism of the present invention is a recombinant microorganism acquiring butanol production capacity obtained by introducing the acetoacetyl-CoA synthase gene encoding an enzyme capable of synthesizing acetoacetyl-CoA from malonyl-CoA and acetyl-CoA and a group of genes involved in butanol biosynthesis that enables synthesis of butanol from acetoacetyl-CoA into a host microorganism.

Acetoacetyl-CoA Synthase Gene

The acetoacetyl-CoA synthase gene is a gene encoding an enzyme having the activity of synthesizing acetoacetyl-CoA from malonyl-CoA and acetyl-CoA and having no activity of synthesizing acetoacetyl-CoA from two acetyl-CoA molecules. This acetoacetyl-CoA synthase gene has been found in, for example, an actinomycete of the genus *Streptomyces* (JP Patent Publication (Kokai) No. 2008-61506 A). For example, a gene derived from an actinomycete of the genus *Streptomyces* can be used.

An example of such acetoacetyl-CoA synthase gene is a gene encoding a protein having the amino acid sequence of SEQ ID NO: 1. Such a protein having the amino acid sequence of SEQ ID NO: 1 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules, which has been found in an actinomycete of the *Streptomyces* sp. CL190 strain (JP Patent Publication (Kokai) No. 2008-61506 A).

The gene encoding a protein having the amino acid sequence of SEQ ID NO: 1 can be obtained by a nucleic acid amplification method (e.g., PCR) with the use of genomic DNA obtained from an actinomycete of the *Streptomyces* sp. CL190 strain as a template and a pair of primers that can be designed with reference to JP Patent Publication (Kokai) No. 2008-61506 A.

In addition, in the present invention, an acetoacetyl-CoA synthase gene is not limited to a gene encoding a protein having the amino acid sequence of SEQ ID NO: 1 from an actinomycete of the *Streptomyces* sp. CL190 strain. It may be a gene encoding a protein having an amino acid sequence highly similar to the amino acid sequence of SEQ ID NO: 1 and having the function of synthesizing acetoacetyl-CoA from malonyl-CoA and acetyl-CoA. The expression "highly similar" used herein refers to, for example, an 80% or more identity, preferably a 90% or more identity, more preferably a 95% or more identity, and most preferably 97% or more identity. Herein, the identity value corresponds to the percentage of identity between amino acid residues in a different amino acid sequence and the amino acid sequence of SEQ ID NO: 1, which is calculated by performing alignment of the amino acid sequence of SEQ ID NO: 1 and the different amino acid sequence with the use of a program for searching for a sequence similarity (also referred to as homology search program in some cases).

Further, in the present invention, the acetoacetyl-CoA synthase gene may be a gene encoding a protein having an amino acid sequence derived from the amino acid sequence of SEQ ID NO: 1 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

Further, in the present invention, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO: 1 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. 2×SSC. Hybridization can be carried out by conventionally known methods such as the method described in J. Sambrook et al. Molecular Cloning, A Laboratory Manual, 2nd Ed., Cold Spring Harbor Laboratory (1989).

A gene encoding an acetoacetyl-CoA synthase having an amino acid sequence that differs from the amino acid sequence of SEQ ID NO: 1 as described above can be isolated from, for example, an actinomycete that is not obtained from the *Streptomyces* sp. CL190 strain. In addition, such gene can be obtained by modifying a polynucleotide encoding the amino acid sequence of SEQ ID NO: 1 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO: 1 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein to be evaluated has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Group of Genes Involved in Butanol Biosynthesis

The term "group of genes involved in butanol biosynthesis" refers to a group consisting of a plurality of genes encoding enzymes involved in the metabolic pathway in which acetoacetyl-CoA is used as a starting compound, thereby carrying out biosynthesis of butanol, which is obtained as a final product. Examples of enzymes involved in the metabolic pathway include β-hydroxybutyryl-CoA dehydrogenase capable of synthesizing 3-hydroxybutyl-CoA with the use of acetoacetyl-CoA as a substrate, 3-hydroxybutyryl-CoA dehydratase capable of synthesizing crotonyl CoA with the use of 3-hydroxybutyl-CoA as a substrate, butyryl-CoA dehydrogenase capable of synthesizing butyryl-CoA with the use of crotonyl CoA as a substrate, butyraldehyde dehydrogenase capable of synthesizing butyraldehyde with the use of butyryl-CoA as a substrate, and butanol dehydrogenase capable of synthesizing butanol with the use of butyraldehyde as a substrate.

The group of genes involved in butanol biosynthesis can be isolated from microorganisms having butanol biosynthesis capacity. As a microorganism having butanol biosynthesis capacity, a microorganism, and particularly, a bacterium having so-called acetone/butanol/ethanol fermentation (ABE fermentation) capacity can be used. A microorganism of the genus *Clostridium* can be used as a microorganism having ABE fermentation capacity. Examples thereof include, but are not particularly limited to, *Clostridium acetobutylicum*, *Clostridium beijerinckii*, *Clostridium saccharoperbutylacetonicum*, *Clostridium saccharoacetobutylicum*, *Clostridium aurantibutyricum*, *Clostridium pasteurianum*, *Clostridium sporogenes*, *Clostridium cadaveris*, and *Clostridium tetanomorphum*. Of these, it is preferable to use, as a microorganism having ABE fermentation capacity, a group of genes involved in butanol biosynthesis from *Clostridium acetobutylicum* and *Clostridium beijerinckii*, in which the total genomic sequence has been elucidated.

In particular, a group of genes from *Clostridium acetobutylicum* involved in butanol biosynthesis is disclosed in detail in Appl. Microbiol. Biotechnol., 77, 1305-1316, 2008. Also in the present invention, the group of genes involved in butanol biosynthesis disclosed in this paper can be used. Specifically, the hbd gene (β-hydroxybutyryl-CoA dehydrogenase gene), the crt gene (3-hydroxybutyryl-CoA dehydratase gene), the bcd gene (butyryl-CoA dehydrogenase gene), and the adhe gene or the adhe1 gene (the butyraldehyde dehydrogenase gene or the butanol dehydrogenase gene) from *Clostridium acetobutylicum* can be used. In addition, the bcd gene exhibits butyryl-CoA dehydrogenase activity when co-expressed with the etfA gene and the etfB gene from *Clostridium acetobutylicum*. Therefore, a group of genes involved in butanol biosynthesis also includes the etfA gene and the etfB gene. Further, the adhe gene and the adhe1 gene encode an enzyme having butyraldehyde dehydrogenase activity and an enzyme having butanol dehydrogenase activity, respectively, which are so-called bifunctional enzymes. Accordingly, when the hbd gene, the crt gene, the bcd gene, and the adhe gene (or the adhe1 gene) from *Clostridium acetobutylicum* are introduced into a host microorganism, the microorganism can acquire the metabolic capacity to synthesize butanol from acetoacetyl-CoA.

Moreover, the above paper discloses the thiolase gene (thiL gene) as a member of a group of genes involved in butanol biosynthesis; thiolase catalyzes a reaction of synthesizing acetoacetyl-CoA from two acetyl-CoA molecules. The group of genes involved in butanol biosynthesis of the present invention may include the thiolase gene but does not necessarily include the thiolase gene.

In addition, the group of genes involved in butanol biosynthesis is not limited to the genes disclosed in the above paper. Genes homologous to the hbd gene, the crt gene, the bcd gene, and the adhe gene (or the adhe1 gene) from *Clostridium acetobutylicum* may be used. Such homologous genes can be identified by homology search such as Blast or Fasta involving the use of a known algorithm in a database containing nucleotide sequences of genes and amino acid sequences of proteins. A homologous gene identified with the use of a database can be isolated from a microorganism by a known method so as to be used. Specifically, nucleic acid fragments containing homologous genes can be obtained by a nucleic acid amplification method with the use of genomic DNA extracted from a microorganism as a template and primers designed based on the nucleotide sequences of the identified homologous genes.

Further, a cDNA library of the aforementioned microorganisms of the genus *Clostridium* having butanol biosynthesis capacity is created by a known method, followed by identification of cDNAs that specifically hybridize with probes designed based on the nucleotide sequences of the hbd gene, the crt gene, the bcd gene, the adhe gene, and the adhe1 gene from *Clostridium acetobutylicum*. Accordingly, the aforementioned homologous genes from microorganisms of the genus *Clostridium* having butanol biosynthesis capacity can be obtained.

In addition, methods for obtaining genes homologous to the hbd gene, the crt gene, the bcd gene, and the adhe gene (or the adhe1 gene) from *Clostridium acetobutylicum* are not limited to the above methods, and therefore any method can be used.

Transformation of a Host Microorganism

The aforementioned "acetoacetyl-CoA synthase gene" and "the group of genes involved in butanol biosynthesis" are incorporated into an adequate expression vector so as to be introduced into a host microorganism. A host microorganism used herein is not particularly limited as long as it can express the genes used in the present invention. Examples thereof include: bacteria belonging to the genus *Escherichia* (e.g., *Escherichia coli*), the genus *Bacillus* (e.g., *Bacillus subtilis*), the genus *Pseudomonas* (e.g., *Pseudomonas putida*), and the genus *Rhizobium* (e.g., *Rhizobium meliloti*); and yeasts such as *Saccharomyces cerevisiae*, *Schizosaccharomyces pombe*, and *Pichia pastoris*.

When a bacterium such as *Escherichia coli* is used as a host, it is preferable for an expression vector to be able to autonomously replicate in such bacterium and to be composed of a promoter, a ribosome binding sequence, the above gene, and a transcription termination sequence. In addition, such an expression vector may contain a gene that controls promoter activity.

As *Escherichia coli*, any conventionally known strain such as the *Escherichia coli* BL21 (DE3) strain, K12 strain, DH1 strain, or JM109 strain can be used. In addition, as *Bacillus subtilis*, the *Bacillus subtilis* 168 strain or the like can be used.

Any promoter may be used as long as it can be expressed in a host such as *Escherichia coli*. Examples of such promoter that can be used include a trp promoter, an lac promoter, a PL promoter, a PR promoter, and the like from *Escherichia coli*, and a T7 promoter from a phage. Further, an artificially designed or modified promoter such as a tac promoter may be used.

A method for introduction of an expression vector is not particularly limited as long as DNA is introduced into a bacterium thereby. Examples thereof include a method using calcium ions [Cohen, S. N., et al.: Proc. Natl. Acad. Sci., USA, 69:2110-2114 (1972)] and an electroporation method.

When a yeast is used as a host, *Saccharomyces cerevisiae*, *Schizosaccharomyces pombe*, *Pichia pastoris*, or the like can be used. In this case, a promoter is not particularly limited as long as it can be expressed in yeast. Examples thereof include a gal1 promoter, a gal10 promoter, a heat-shock protein promoter, an MFα1 promoter, a PHO5 promoter, a PGK promoter, a GAP promoter, an ADH promoter, and an AOX1 promoter.

A method for introducing a recombinant vector into yeast is not particularly limited as long as DNA is introduced into yeast thereby. Examples thereof include the electroporation method [Becker, D. M., et al. Methods. Enzymol., 194: 182-187 (1990)], the spheroplast method [Hinnen, A. et al.: Proc. Natl. Acad. Sci., USA, 75: 1929-1933 (1978)], and the lithium acetate method [Itoh, H.: J. Bacteriol., 153: 163-168 (1983)].

In particular, it is preferable to use, as a host microorganism, a microorganism with a relatively high malonyl-CoA content. Malonyl-CoA is a substance used for biosynthesis of fatty acid and is present in all microorganisms. The aforementioned acetoacetyl-CoA synthase synthesizes acetoacetyl-CoA from malonyl-CoA and acetyl-CoA. Therefore, the butanol productivity can be improved with the use of a host microorganism with a high malonyl-CoA content.

Butanol Production

Butanol biosynthesis is allowed to proceed by culturing the aforementioned microorganism into which "the acetoacetyl-CoA synthase gene" and "the group of genes involved in butanol biosynthesis" have been introduced in a medium containing carbon sources such as glucose. Specifically, pyruvic acid is first produced via biosynthesis in a glycolytic system with the use of carbon sources such as glucose. Then, acetyl-CoA and further malonyl-CoA are produced from pyruvic acid. Further, the aforementioned acetoacetyl-CoA synthase synthesizes acetoacetyl-CoA from acetyl-CoA and malonyl-CoA. Subsequently, the above group of genes involved in butanol biosynthesis synthesizes butanol from acetoacetyl-CoA.

In particular, the acetoacetyl-CoA synthase of the present invention synthesizes acetoacetyl-CoA from malonyl-CoA and acetyl-CoA via an irreversible reaction. Meanwhile, thiolase contributes to a reaction of synthesizing acetoacetyl-CoA from two acetyl-CoA molecules. In this reaction, two acetyl-CoA molecules are necessary for synthesis of acetoacetyl-CoA. In addition, the reaction is a reversible reaction, in which an acetoacetyl-CoA degradation reaction proceeds for the most part. Consequently, the use of acetoacetyl-CoA synthase capable of synthesizing acetoacetyl-CoA from malonyl-CoA and acetyl-CoA results in significant improvement in butanol productivity, compared with the case of butanol biosynthesis with the use of thiolase and a group of genes involved in butanol biosynthesis.

Further, culture conditions for culturing a microorganism into which the aforementioned "acetoacetyl-CoA synthase gene" and "the group of genes involved in butanol biosynthesis" have been introduced are not particularly limited. Therefore, culture can be conducted under general conditions except that a medium appropriate for maintaining auxotrophy and drug resistance of a host microorganism is used under anaerobic conditions.

In addition, since synthesized butanol is present in a medium, butanol can be obtained from a supernatant fraction after separation of cells from a medium by means of centrifugation or the like. In one case, butanol can be isolated from a supernatant fraction by adding organic solvents such as ethyl acetate and methanol to a supernatant fraction and sufficiently agitating the mixture. The mixture is separated into an aqueous phase and a solvent phase, and then butanol can be extracted from the solvent phase.

EXAMPLES

The present invention is hereafter described in greater detail with reference to the following examples, although the technical scope of the present invention is not limited thereto.

Example 1

Preparation of *Clostridium acetobutylicum* Genomic DNA

The *Clostridium acetobutylicum* ATCC (824) strain was subjected to anaerobic culture at 30° C. for 2 days in a *Clostridium* enrichment medium (Difco) (3 ml) according to a general method. Genomic DNA was prepared from the culture solution (1.5 ml) with the use of a genomic DNA preparation kit (Gentra Puregene Yeast/Bact. kit) (QIAGEN).

Preparation of pT7Blue-CAC2873

The thiA gene, which is a thiolase gene from the *Clostridium acetobutylicum* ATCC (824) strain, was cloned as described below. First, the following primers were used for PCR.

```
CAC2873-F:
                                       (SEQ ID NO: 2)
5'-ATG AAA GAA GTT GTA ATA GCT AGT GCA G-3'

CAC2873-R:
                                       (SEQ ID NO: 3)
5'-CTA GCA CTT TTC TAG CAA TAT TGC TG-3'
```

The genomic DNA (0.1 μg) of the *Clostridium acetobutylicum* ATCC (824) strain prepared above was used as a template for PCR. In addition, each of primers of the above primer pair was used in an amount of 50 pmol. Regarding the reaction solution composition, a solution (50 μl) comprising 1×Pfu Ultra II reaction buffer (Stratagene) containing dNTP (10 nmol) and Pfu Ultra II fusion HS DNA polymerase (Stratagene) (1 μl) was used. PCR thermal cycles were as follows: 95° C. for 5 minutes; 30 cycles of 95° C. for 30 seconds, 60° C. for 30 seconds, and 72° C. for 3 minutes; and 72° C. for 3 minutes. Further, the resulting solution was stored as a stock solution at 4° C. after the completion of the reaction.

A fragment amplified by PCR (approximately 1.2 kb) was subjected to blunt-end cloning into a pT7-Blue vector with the use of a Perfectly Blunt Cloning Kit (Novagen). The cloned sequence was subjected to sequencing such that the sequence was confirmed to correspond to the thiA gene of the *Clostridium acetobutylicum* ATCC (824) strain. The thus obtained plasmid was named pT7Blue-CAC2873.

Preparation of pCDFDuet-thiA

An expression vector for causing expression of the above thiA gene in *Escherichia coli* was constructed as described below. First, PCR was carried out with the use of the following primers.

```
acat-NdeI-F:
                                       (SEQ ID NO: 4)
5'-AAA CAT ATG AAA GAA GTT GTA ATA GC-3' acat-XhoI-R:
                                       (SEQ ID NO: 5)
5'-AAA CTC GAG CTA GCA CTT TTC TAG CAA T-3'
``` pT7Blue-CAC2873 prepared above was used as a template for PCR. In addition, each of primers of the above primer pair was used in an amount of 10 pmol. Regarding the reaction solution composition, a solution (50 µl) comprising 1×Pfu Ultra™II reaction buffer (Stratagene) containing dNTP (12.5 nmol) and a Pfu Ultra™II fusion HS DNA polymerase (Stratagene) (1 µl) was used. PCR thermal cycles were as follows: 95° C. for 2 minutes; 5 cycles of 95° C. for 20 seconds, 43° C. for 20 seconds, and 72° C. for 40 seconds; 30 cycles of 95° C. for 20 seconds, 50° C. for 20 seconds, and 72° C. for 40 seconds; and 72° C. for 3 minutes. Further, the resulting solution was stored as a stock solution at 4° C. after the completion of the reaction.

A DNA fragment amplified by PCR (approximately 1.2 bp) was purified with a MinElute PCR Purification Kit and cloned into a pCR-Blunt II-Topo vector with the use of a Zero Blunt TOPO PCR Cloning Kit. The thus obtained vector was named pCR-Blunt II-TOPO-thiA. pCR-Blunt II-TOPO-thiA was cleaved with NdeI and XhoI. A DNA fragment (approximately 1.2 Kbp) was purified by agarose gel electrophoresis and then inserted into the NdeI-XhoI site of pCDF-Duet (Novagen). The obtained plasmid was designated as pCDF-Duet-thiA.

Preparation of pCDFDuet-orfN

The acetoacetyl-CoA synthase gene capable of synthesizing acetoacetyl-CoA was cloned from malonyl-CoA and acetyl-CoA as described below. First, PCR was carried out with the use of the following primers.

```
OrfN-NdeI-F:
                                    (SEQ ID NO: 6)
5'-AAA CAT ATG ACC GAC GTC CGA TTC CGC AT 3'

OrfN-XhoI-R:
                                    (SEQ ID NO: 7)
5'-AAA CTC GAG TTA CCA CTC GAT CAG GGC GA 3'
``` pHISORFn (20 ng) was used as a template for PCR. pHISORFn described in JP Patent Publication (Kokai) No. 2008-61506 A was used. In addition, each of primers of the above primer pair was used in an amount of 15 pmol. Regarding the reaction solution composition, a solution (50 µl) comprising 1× PrimeSTAR GC Buffer (Mg$^{2+}$ plus) (TAKARA Bio Inc.) containing dNTP (10 nmol) and PrimeSTAR HS DNA Polymerase (TAKARA Bio Inc.) (0.5 µl) was used. PCR was carried out with the following thermal cycles: 94° C. for 1 minute; 5 cycles of 98° C. for 10 seconds, 53° C. for 5 seconds, and 72° C. for 1 minute; 30 cycles of 98° C. for 10 seconds, 60° C. for 5 seconds, 72° C. for 1 minute; and 72° C. for 5 minutes. Further, the resulting solution was stored as a stock solution at 4° C. after the completion of the reaction.

A DNA fragment amplified by PCR (approximately 1 Kbp) was purified with a MinElute PCR Purification Kit and cloned into a pCR-Blunt II-Topo vector with the use of a Zero Blunt TOPO PCR Cloning Kit. The obtained vector was named pCR-Blunt II-TOPO-orfN. pCR-Blunt II-TOPO-orfN was cleaved with NdeI and XhoI. A DNA fragment (approximately 1 Kbp) was purified by agarose gel electrophoresis and then inserted into the NdeI-XhoI site of pCDF-Duet (Novagen). The obtained plasmid was designated as pCDF-Duet-orfN.

Preparation of pETDuet-crt-bcd-etfB-etfA-hbd

An operon comprising the crt gene, the bcd gene, the etfB gene, the etfA gene, and the hbd gene of a group of genes involved in butanol biosynthesis for the *Clostridium acetobutylicum* ATCC (824) strain was cloned as described below. PCR was carried out with the use of the following primers.

```
crt-NcoI-F:
                                    (SEQ ID NO: 8)
5'-CTC CCA TGG AAC TAA ACA ATG TCA TCC TTG-3' crt-BamHI-R:
                                    (SEQ ID NO: 9)
5'-AAC GGA TCC TTA TTT TGA ATA ATC GTA GAA ACC TTT
TC-3'
```

The genomic DNA of the *Clostridium acetobutylicum* ATCC (824) strain prepared above (0.02 µg) was used as a template for PCR. Regarding the reaction solution composition, the composition of a reaction solution (50 µl) containing dNTP (12.5 nmol) and Pfu UltraII (Stratagene) (1 µl) was used. For PCR thermal cycles, 28 cycles of a denaturation reaction step at 95° C. for 20 seconds, an annealing step at 53° C. for 20 seconds, and an elongation reaction step at 72° C. for 120 seconds were carried out. Further, the resulting solution was stored as a stock solution at 4° C. after the completion of the reaction.

DNA amplified by PCR was cleaved with NcoI and BamHI and subjected to agarose gel electrophoresis, followed by purification of a 4500-bp DNA fragment. This fragment was inserted into the NcoI/BamHI site of pET-Duet (Merk). The cloned sequence was subjected to sequencing such that the sequence was confirmed to correspond to the crt-bcd-etfA-etfB-hbd operon sequence of the *Clostridium acetobutylicum* ATCC (824) strain. The obtained plasmid was designated as pETDuet-crt-bcd-etfB-etfA-hbd.

Preparation of pETDuet-crt-bcd-etfB-etfA-hbd-adhe

The adhe gene, which is a member of a group of genes involved in butanol biosynthesis from the *Clostridium acetobutylicum* ATCC (824) strain, was cloned as described below. First, PCR was carried out with the use of the following primers.

```
adhe-SalI-F:
                                    (SEQ ID NO: 10)
5'-CAC GTC GAC AAG GAG ATA TAA TGA AAG TTA CAA ATC
AAA AAG AAC TA-3' adhe-NotI-R:
                                    (SEQ ID NO: 11)
5'-CAC GCG GCC GCT AAA AAT GAT TTT ATA TAG ATA TCC
TTA AGT TCA C-3'
```

The genomic DNA of the *Clostridium acetobutylicum* ATCC (824) strain prepared above (0.1 µg) was used as a template for PCR. Regarding the reaction solution composition, the composition of a reaction solution (50 µl) containing primers (15 pmol each), dNTP (12.5 nmol), and Prime STAR HS (TakaraBio) (1 µl) was used. For PCR thermal cycles, 28 cycles of a denaturation reaction step at 95° C. for 20 seconds, an annealing step of 53° C. for 20 seconds, and an elongation reaction step of 72° C. for 120 seconds were carried out. Further, the resulting solution was stored as a stock solution at 4° C. after the completion of the reaction.

DNA amplified by PCR was cleaved with SalI and NotI and subjected to agarose gel electrophoresis, followed by purification of a 2500-bp DNA fragment. This DNA fragment was inserted into the multi cloning site (SalI/NotI site) of pET-Duet-crt-bcd-etfB-etfA-hbd prepared above. The cloned sequence was subjected to sequencing such that the sequence was confirmed to correspond to the adhe sequence of the *Clostridium acetobutylicum* ATCC (824) strain. The obtained plasmid was named pETDuet-crt-bcd-etfB-etfA-hbd-adhe.

Preparation of Recombinant *Escherichia coli*

The above prepared plasmid pETDuet-crt-bcd-etfB-etfA-hbd-adhe and pCDFDuet-thiA or pCDFDuet-orfN were introduced into an *Escherichia coli* Tuner strain (TAKARA Bio Inc.). The obtained recombinant *Escherichia coli* products were named pCDFDuet-thiA/pETDuet-crt-bcd-etfB-etfA-hbd-adhe/Tuner and pCDFDuet-orfN/pETDuet-crt-bcd-etfB-etfA-hbd-adhe/Tuner.

Culture of Recombinant *Escherichia coli*

The recombinant *Escherichia coli* pCDFDuet-thiA/pETDuet-crt-bcd-etfB-etfA-hbd-adhe/Tuner and pCDFDuet-orfN/pETDuet-crt-bcd-etfB-etfA-hbd-adhe/Tuner obtained above were cultured in an LB medium or an M9 medium containing glucose at 4% and/or thiamine at 0.0001% (each at final concentration), to which antibiotics (ampicillin, tetracycline, and/or streptomycin) had been added according to need.

An LB medium (4 ml) contained in a 12-ml disposable tube (Falcon) was inoculated with a recombinant *Escherichia coli* colony, followed by overnight shake culture at 30° C. Further, an LB medium (20 ml) contained in a 50-ml disposable tube (Corning Incorporated) was inoculated with the culture solution (0.2 ml), followed by overnight shake culture at 30° C. After culture, determination was carried out at 660 nm (OD). The tube used for culture was subjected to centrifugation at 4° C. and 8000 g for 10 seconds. The supernatant was discarded via decantation and the tube was transferred to an anaerobic box. An M9 medium preliminarily stored in an anaerobic box was added thereto so as to result in an absorbance of 12 to 15 at 660 nm (OD), followed by sufficient suspension. IPTG was added thereto to a final concentration of 10 μM, followed by suspension. The resultant was transferred to a disposable test tube. The tube was covered with an aluminium cap, followed by anaerobic static culture at 30° C. for 24 hours.

<Butanol Analysis>

After the completion of culture, the test tube was removed from the anaerobic box. The culture solution was dispensed into Eppendorf tubes, followed by centrifugation at 14000 rpm for 5 minutes with the use of a centrifuge (TOMY). Thus, the supernatant was separated from the cells. A portion of the supernatant (1 ml) was transferred into a disposable test tube. Ethyl acetate (1 ml) and methanol (0.3 ml) were added thereto, followed by agitation for 10 minutes with a vortex mixer in a draft. The solvent phase and the aqueous phase were separated from each other via centrifugation at room temperature and 1200 rpm for 5 minutes with a centrifuge (Beckman Coulter, Inc.). The solvent phase was transferred to a GC/MS vial bottle to which a 1% undecanol solution (dis-solved in ethanol) (10 μl) had been added as an internal control. Then, butanol was quantitatively analyzed by GC/MS.

An HP6890/5973 GC/MS system (Hewlett-Packard) was used for GC/MS. The column used was a J&W DB-624 column (0.32 mm×60 m; film thickness: 1.8 μm). GC/MS analysis conditions were as follows.

Inlet temperature: 260° C.
Detector temperature: 260° C.
Injection parameters: Automatic injection mode
Sample volume: 2 μl
Methanol washing (3 times) and chloroform washing (2 times)
Split ratio: 1/20
Carrier gas: Helium gas (1.0 ml/minute)
Oven heating conditions: 70° C. for 5 minutes, heating to 130° C. (10° C./minute), and heating to 260° C. (100° C./minute).
Internal standard: 1-undecanol (0.01 μl in ethanol)
Confidence standard: Butanol (nacalai tesque)

Butanol was quantified by GC/MS under the above conditions. At this time, the amount of butanol contained in the culture solution was calculated based on the peak area ratio of the confidence standard to the internal standard. Table 1 lists the results.

TABLE 1

|  | Butanol (mg/L) |
| --- | --- |
| Medium alone | 0.0 |
| Tuner strain | 0.0 |
| pETDuet-crt-bcd-etfB-etfA-hbd-adhe/Tuner | 0.0 |
| pCDFDuet-thiA/pETDuet-crt-bcd-etfB-etfA-hbd-adhe/Tuner | 4.7 |
| pCDFDuet-orfN/pETDuet-crt-bcd-etfB-etfA-hbd-adhe/Tuner | 7.2 |

As shown in table 1, even though a group of genes involved in butanol biosynthesis from the *Clostridium acetobutylicum* ATCC (824) strain was exclusively introduced into *Escherichia coli*, butanol was not detected or detected at a minute amount. Meanwhile, when a group of genes involved in butanol biosynthesis derived from the *Clostridium acetobutylicum* ATCC (824) strain and the thiolase gene or the acetoacetyl-CoA synthase gene capable of synthesizing acetoacetyl-CoA from malonyl-CoA and acetyl-CoA were introduced into recombinant *Escherichia coli*, it was possible to produce butanol.

In particular, the amount of butanol produced in the recombinant *Escherichia coli* into which the acetoacetyl-CoA synthase gene had been introduced was significantly greater than that in the case of the recombinant *Escherichia coli* into which the thiolase gene had been introduced. Based on the above results, the following novel finding could be obtained: when a group of genes involved in butanol biosynthesis is used for butanol biosynthesis, synthesis of acetoacetyl-CoA with acetoacetyl-CoA synthase capable of synthesizing acetoacetyl-CoA from malonyl-CoA and acetyl-CoA is superior to synthesis of acetoacetyl-CoA with thiolase in terms of the butanol production efficiency.

Sequence Listing
90217043731803_0012009113632_100002.app

What is claimed is:

1. A recombinant microorganism, comprising an acetoacetyl-CoA synthase gene encoding a protein having the amino acid sequence of SEQ ID NO: 1, and a group of genes from *Clostridium acetobutvlicum* that are involved in butanol biosynthesis that enables synthesis of butanol from acetoacetyl-CoA, wherein the genes are introduced into a host microorganism, wherein the group of genes involved in butanol biosynthesis consists of the β-hydroxybutyryl-CoA dehydrogenase gene, the 3-hydroxybutyryl-CoA dehydratase gene, the butyryl-CoA dehydrogenase gene, the butyraldehyde dehydrogenase gene, and the butanol dehydrogenase gene, wherein the acetoacetyl-CoA synthase gene is a gene from an actinomycete of the genus *Streptomyces*, and wherein the host microorganism is *Escherichia coli*.

2. A butanol production method, comprising steps of:
culturing a recombinant microorganism according to claim 1 in a culture medium; and
collecting butanol from the medium.

* * * * *